United States Patent [19]

Hoffmann

[11] 4,033,756

[45] July 5, 1977

[54] DICHLOROACETAMIDE TREATED RICE SEEDS

[75] Inventor: Otto L. Hoffmann, Shawnee, Kans.

[73] Assignee: Gulf Research & Development Company, Pittsburgh, Pa.

[22] Filed: Sept. 17, 1971

[21] Appl. No.: 181,580

[52] U.S. Cl. .................. 71/118; 71/88; 71/90; 71/94; 71/95; 71/100; 71/111; 71/115; 71/117; 71/121; 260/239 BF; 260/247.7 V; 260/287 D; 260/290 HL; 260/293.86; 260/305; 260/326.8; 260/340.9; 260/347.3; 260/471 K; 260/558 P; 260/558 R; 260/558 S; 260/558 H; 260/561 HL; 260/562 B; 260/562 P; 260/562 H

[51] Int. Cl.² .......................... A01N 9/20

[58] Field of Search ............... 71/77, 79, 100, 118

[56] References Cited

UNITED STATES PATENTS 3,131,509  5/1964  Hoffman ................. 71/77 X

*Primary Examiner*—Glennon H. Hollrah
*Attorney, Agent, or Firm*—Carl A. Cline

[57] ABSTRACT

Crop seed, particularly corn, grain sorghum and rice are protected from injury by a variety of herbicides particularly the thiocarbamates and some amide types by coating thereon a small, non-phytotoxic amount of an N-substituted amide of a chloro or bromo alkanoic acid, preferably an N-substituted dichloroacetamide.

1 Claim, No Drawings

DICHLOROACETAMIDE TREATED RICE SEEDS

DESCRIPTION OF THE INVENTION

In U.S. Pat. No. 3,131,509 there is disclosed the coating of crop seeds with a non-phytotoxic quantity of a chemical which is antagonistic to a selective herbicide, thereby protecting the crop from injury when the specific herbicide is employed to control weeds. The aforementioned patent specifically exemplifies the treatment of wheat sed with compounds which are antagonistic to barban and to certain thiocarbamate herbicides. Among the useful antagonistic agents which are disclosed are m-chlorotribromoacetanilide and 2,4'-dichloropropionanilide.

In U.S. Pat No. 3,564,768 there is disclosed the use of several compounds to coat corn seed to render it resistant to thiocarbamate herbicides. In particular, 1,8-naphthalic anhydride is disclosed to be useful in protecting corn against EPTC, which is a very well known and highly effective thiocarbamate herbicide.

I have now discovered that amides of chloro and bromo substituted alkanoic acids having from two to four carbon atoms constitute a class of compounds, some members of which are superior to any previously known chemical agents used for the purposes of protecting seed from herbicides. Because the previously employed haloalkanoamides suffered from certain defects such as phytotoxicity, the possibility of superior performance of compounds of related classes was not suspected. In tests of over a thousand haloalkanoamides it has been found that over 40% are effective and safe for use in protecting such crop seeds as corn, grain sorghum and rice from a rather large group of thiocarbamate and amide herbicides which are commonly used in pre-emergent control of weeds. About one fourth of the amides of 2-chloropropionic acid, dibromoacetic acid, phenylchloroacetic acid and 3-chloropropionic acid are also quite effective and safe to use for this purpose, although they may suffer from certain other disadvantages, as disclosed herein. The amides may be applied to crop seed by mixing the seed thoroughly with an aqueous dispersion, methanol solution or other formulation of the active chemical, preferably with a diluent, so that a small percentage of the chemical, usually less than 3% by weight, is distributed on the surface of the seeds in a substantially uniform manner. In some instances the dry chemical is readily distributed uniformly without a diluent. Examples of the compounds which are proved to be superior to any seed treating agent previously disclosed are those listed below in Groups 1 to 8. For convenience they are classified according to the acyl substituent, and are listed by the amine employed to synthesize the amide.

The dichloroacetamides are the preferred group because to general superiority with respect to both effectiveness and safety. Illustrative compounds are listed in Group 1.

| GROUP 1 - DICHLOROACETAMIDES | |
|---|---|
| Amine | Preferred Rate of Application |
| Dipropylamine | 1/16 wt. percent |
| Allylamine | 1 |
| Propargylamine | 1/2 |
| 1,3-Dipentylamine | 1/8 |
| Isobutylamine | 1/32 |
| t-Butylamine | 1/8 |
| Dipropargylamine | 1/16 |
| Diisobutylamine | 1/8 |
| Cyclohexylamine | 1/2 to 3 |
| Cyclopropylamine | 1/8 |
| 3-Methylisoquinoline | 1/16 |
| N-Ethylaniline | 1/16 |
| Isopentylamine | 1/4 |
| 2-Aminobenzotrifluoride | 1/2 |
| Propylamine | 1/4 |
| n-Butylamine | 1/64 |
| 2-Ethylhexylamine | 1/2 |
| 1-Naphthylamine | 1 |
| Diethylamine | 1/2 |
| Methylamine | 1 |
| 2-Amino-4-chlorobenzothiazole | 1/4 |
| 2-Amino-1-methoxypropane | 1/2 |
| 2-Amino-3,3-dimethylbutane | 1/4 |
| 2-Ethylpiperidine | 1/4 |
| 2,5-Dimethylpyrrolidine | 1/2 |
| Tetrahydrofurfurylamine | 1/2 |
| Ethylenediamine | 1 |
| o-Phenylenediamine | 1/4 |
| 4-Chloro-m-phenylenediamine | 1 |
| 1,6-Hexanediamine | 1/8 |
| Isopropylamine | 1/4 |
| 3-Chloro-2-methylaniline | 1/8 |
| Ethanolamine | 1 |
| o-Toluidine | 1 |
| 2,6-Dichloroaniline | 1/4 |
| Pyrrolidine | 1/32 |
| Piperidine | 1/2 |
| Aniline | 1/8 |
| o-Chloro-N-methylbenzylamine | 1/2 |
| 4-Aminomethylpyridine | 1 |
| 1,8-Diaminonaphthalene | 1/4 |
| m-Aminophenol | 1/8 |
| 4-Chloro-2,5-dimethylaniline | 1 |
| 3-Chloro-4-methoxyaniline | 1 |
| 4-Chloro-2-methylaniline | 1/4 |
| 2-Amino-5-picoline | 1/8 |
| p-Bromoaniline | 1/2 |
| N-allylaniline | 1/4 |
| N-allyl-o-toluidine | 1/16 |
| o-Aminobenzylalcohol | 1/2 |
| 3-Aminothiophenol | 1 |
| 2-(Benzyloxy)-ethylamine | 1/8 |
| 2,5-Dimethylpyrrole | 1 |
| N-Isopropylbenzylamine | 1/4 |
| N-Methylbutylamine | 1/2 |
| 3-Isopropoxypropylamine | 1 |
| N-Methyl methyl anthranilate | 1/4 |
| N-Ethyl-o-toluidine | 1/8 |
| 3-Chloro-p-toluidine | 1/2 |
| N-Isopropylcyclohexylamine | 1/4 |
| 3-Methylmercaptoaniline | 1/8 |
| 2-Methyl-4-nitroaniline | 1 |
| N-Ethyl-m-toluidine | 1/16 |
| 2,4-Diaminotoluene | 1/2 |
| Benzoylhydrazide | |
| 2-Amino-p-cymene | 1/8 |
| 2-Amino-5-chloropyridine | 1/8 |
| Cyclobutylamine | 1/4 |
| 3-Amino-4-chlorobenzotrifluoride | 1/2 |
| 2,3-Diaminopyridine | 1/2 |
| 4-Iodoaniline | 1/4 |
| 3-Fluoroaniline | 1/4 |
| 3-Iodoaniline | 1/4 |
| 4,5-Dichloro-o-phenylenediamine | 1/4 |
| Furfurylamine | 1/16 |
| 2-Ethylaniline | 1/8 |
| 1-Amino-5,6,7,8-tetrahydronaphthalene | 1 |
| 4-Methoxy-2-methylaniline | 1/4 |
| N-Methyltetrahydrofurfurylamine | 1/8 |
| 2-Methoxy-5-methylaniline | 1 |
| 2,5-Dimethoxyaniline | 1 |
| 4-Methoxy-2-nitroaniline | 1/2 |
| Morpholine | 1/8 |
| N-Ethyl-1-naphthylamine | 1 |
| 2-Ethylhexylamine | 1/2 |
| Ethylamine | 1/4 |
| 1-α-(1-Naphthyl)ethylamine | 1/4 |
| 2,4,6-Trimethylpiperidine | 1/4 |
| m-Toluidine | 1/8 |
| p-Phenoxyaniline | 1 |
| m-Nitroaniline | 1/8 |
| 2,2,6,6-Tetramethylpiperidine | 1/4 |
| 1,2,3,4-Tetrahydroisoquinoline | 1/2 |
| Benzylamine | 1/2 |
| Diisopentylamine | 1/4 |
| dl-α-Methylbenzylamine | 1/2 |
| 4-Chlorobenzylamine | 1/2 |

GROUP 1 - DICHLOROACETAMIDES

| Amine | Preferred Rate of Application |
|---|---|
| N-Benzylmethylamine | 1/8 |
| 2,6-Dimethylphenylamine | 1 |
| 3,4-Dichlorobenzylamine | 1/2 |
| Cycloheptylamine | 1/2 |
| Heptamethyleneimine | 1 |
| Dimethylamine | 1/2 |
| N-Ethylaniline | 1/8 |
| Dibutylamine | 1/2 |
| N-Methylbutylamine | 1/4 |
| Phenethylamine | 1/2 |
| Dibenzylamine | 1/2 |
| 2,4-Dichlorobenzylamine | 1/2 |
| 3-Chlorobenzylamine | 1/2 |
| N-Cyclohexylmethylamine | 1/2 |
| Aniline | 1/2 |
| 1-(−)-α-Methylbenzylamine | 1/2 |
| t-Butylamine | 1/2 |
| 2,5-Dichloroaniline | 3 |

The trichloroacetamides as a class are inclined to produce phytotoxic side effects, the symptoms of which resemble effects produced by the thiocarbamate herbicides. Careful adjustment of application rate alleviates this problem. Illustrative superior compounds are listed in Group 2.

GROUP 2 - TRICHLOROACETAMIDES

| Amine | Preferred Rate of Application |
|---|---|
| Cyclohexylamine | 1/2 wt. percent |
| Isobutylamine | 1/8 |
| Cyclopropylamine | 1/2 |
| 3-Methylisoquinoline | 1/4 |
| 4-Chlorobenzylamine | 1/4 |
| Cycloheptylamine | 1/4 |
| Diisopentylamine | 1/4 |
| Dimethylamine | 1/16 |
| 1-(−)-α-Methylnaphthylene Diethylamine | 1/4 |
| 4-Aminomethylpyridine | 1 |
| 2,5-Dimethylpyrrolidine | 1/2 |
| o-Chloro-N-methylbenzylamine | 1/8 |
| 2,5-Dimethylpyrrole | 1/8 |
| N-Methylbutylamine | 1/8 |
| 3-Diethylaminopropylamine | 1 |
| 1-Amino-5,6,7,8-tetrahydronaphthalene | 1/2 |
| 2,4,6-Trimethylpiperidine | 1 |
| Benzylamine | 1/4 |
| 3-Chlorobenzylamine | 1/2 |
| n-Benzylmethylamine | 1/2 |
| Heptamethyleneimine | 1/2 |
| 2,6-Diethylaniline | 1/2 |

Among miscellaneous haloalkanoamides which are also superior are the illustrative compounds of Groups 3 and 4.

GROUP 3 - 2-BROMOISOBUTYRAMIDES

| Amine Group | Preferred Rate of Application |
|---|---|
| Dipropargylamine | 1/2 wt. percent |
| α-Methylbenzylamine | 3 |

GROUP 4 - 2-BROMOBUTRYAMIDES

| Amine Group | Preferred Rate of Application |
|---|---|
| Dipropargylamine | 1/8 wt. percent |
| Methylamine | 1/2 |

| Amine Group | Preferred Rate of Application |
|---|---|
| N-Methyltetrahydrofurfurylamine | 1/2 |

The 2- and 3-chloropropionamides in general show some tendency toward phytotoxicity, are not as persistent and may migrate away from the treated seed in time. Nevertheless, a few higher molecular weight chloropropionamides are superior to previously disclosed compounds for protecting corn seed, as illustrated by those listed in Groups 5 and 6

GROUP 5 - 2-CHLOROPROPIONAMIDES

| Amine Group | Preferred Rate of Application |
|---|---|
| 1-α-(1-naphthyl)-ethylamine | 1/4 wt. percent |
| 2,4,6-Trimethylaniline | 1/8 |
| 2,4,5-Trimethylaniline | 1 |
| 2,4,6-Trimethylpiperidine | 1/4 |
| 1,1,3,3-Tetramethylbutylamine | 1/2 |

GROUP 6 - 3-CHLOROPRIOPIONAMIDES

| Amine Group | Preferred Rate of Application |
|---|---|
| Diisopropylamine | 1/2 wt. percent |
| p-Bromo-α-methylbenzylamine | 1/2 |
| piperonylamine | 1/2 to 3 |

Tribromoacetamides and 2,2-dichloropropionamides are also useful seed treating agents, as illustrated by the compounds listed in Groups 7 and 8.

GROUP 7 - TRIBROMOACETAMIDES

| Amine Group | Preferred Rate of Application |
|---|---|
| α-Methylbenzylamine | 1/2 − 3 wt. percent |
| Benzylamine | 3 |
| Isopropylamine | 1/2 |
| Butylamine | 1/2 to 3 |
| Dimethylamine | 3 |
| N-Methylbenzylamine | 3 |
| Tetrahydrofurfurylamine | 1/2 |
| 2,4,6-Trimethylpiperidine | 3 |

GROUP 8 - 2,2-DICHLOROPROPIONAMIDES

| Amine Group | Preferred Rate of Application |
|---|---|
| 4-Methoxybenzylamine | 1/2 wt. percent |
| 4-Chlorobenzylamine | 1/2 |
| α-Methylbenzylamine | 1/2 |
| 4-Chloro-α-methylbenzylamine | 1/2 |
| Isopentylamine | 1/2 |
| Tertiary amylamine | 3 |
| Heptamethyleneimine | 3 |
| N-Methylbenzylamine | 1/2 |
| Ethylenediamine | 1/2 to 3 |

The chemical protection of crop seeds from herbicides, to be economically attractive, involves several factors which must be taken into consideration. It will be appreciated that the chemical treating agent should be a substance which will remain in close contact with the crop seeds for a sufficient length of time to protect the emerging crop plants until an dangerous concentration of herbicide is no longer present. I have discovered that some compounds, probably because of water solubility or an ability to diffuse, appear to migrate away from the crop seed over a period of time. Some of these compounds evidently disappear, others apparently begin to protect nearby seeds of weeds and volunteer grains of crop plants. This is a severe disadvantage because it reduces the effectiveness of herbicides within the row of the crop, where wed control is the most difficult and the most important. Other compounds have a tendency to exert phytotoxic effects on the crop plant itself. This may occur in three ways, prevention of emergence of the crop so that germination appears to be poor, production of abnormal forms of growth in the emerging crop plants and stunting or retarding of the growth of crop plants. In some instances these effects may be alleviated satisfactorily by simply reducing the rate of application. In other instances it does not appear feasible to use the compounds at a low enough rate to reduce the injury to an economically acceptable level. In some instances the chemical treating agents will protect the crop from the use of conventional amounts of herbicides but where there are occasional overdoses such as by the overlapping of spray patterns, the compounds fail to protect. For commercial use it is very desirable to protect the crop seeds from about twice the intended level of herbicide use because of these occasional overdoses from overlapping treating zones. Otherwise, replanting of some areas in the field will be required.

SYNTHESIS OF AMIDES

Chemicals employed in the method of this invention may be made by reacting one molar equivalent of the acid chloride with two molar equivalents of the amine (one molar equivalent of diamines). For the preparation of small amounts in the laboratory, the reaction may be carried out in ether. After reaction the ether is evaporated and the chemicals may be used without further purification. In some instances the amine hydrochloride is preferably removed from the reaction mixture, but this step is not essential to demonstrate the beneficial effect of most of the chemicals. A description of the simple procedure for amide synthesis in ether solution is found in *Journal of the Indian Chemical Society*, vol. 25, pages 483–484 (1948).

An efficient procedure which yields purified amides is found in *Journal of Medicinal Chemistry* vol. 9, pages 704–707 (1966). A procedure employed to prepare many of the amides is presented below by way of illustration.

PREPARATION OF N-CYCLOPROPYLDICHLOROACETAMIDE

To a solution of cyclopropylamine (28.6 g, 0.5 mol) and 50 ml of triethylamine in 200 ml of anhydrous benzene was added dropwise with stirring and ice-bath cooling dichloroacetyl chloride (73.7 g, 0.5 mol). The solution was stirred 2 hr at room temperature. The benzene solution was washed successively with 10% HCl, $H_2O$ and saturated NaCl solution and dried over anhydrous $MgSO_4$. The solvent was distilled affording 68.3 g (82%) of white crystalline product, m.p. 125–7¼. Recrystallization from ethanol-benzene yielded purified product; m.p. 130°–2°.

CHEMICAL PROTECTION OF SEEDS FROM HERBICIDES

Crop seeds are treated by shaking or tumbling the chemical with the crop seed. A sticker or spreading agent can be added to the chemical to enhance adherence and coverage of the seed.

Alternately the chemicals of this invention can be dissolved or suspended in water customarily used to soak certain crop seeds prior to germination. A surfactant can be used to enhance suspension of the chemical in water and penetration of the chemical into the crop seed.

A. Protection of Corn Seed

Comparative evaluation of seed-treating agents may be accomplished in the greenhouse by means of the following procedure.

To 5.0 grams of single cross corn seed in a 3 dram vial is added 3% (150 mg) of the test chemical and 0.1 ml (2% methanol. The vial is capped and shaken for 2 seconds in a Spex mixer. Five seeds are planted in a flat of greenhouse soil and lightly covered. EPTC (ethyl, N,N-di-propylthiolcarbamate) is applied at a rate of 24 lbs/A. It is covered with soil and the flat is watered. In each flat are two rows of untreated and four rows of treated corn. When control corn (no herbicide) is 50 cm. tall, the treatments are rated according to the following system. Each treatment is rated according to the number of plants emerged (0–5) the number distorted by EPTC (0–5) and the height. Height is given the following numerical value: 0 = no plants, 1 is 5 cm or less and is equivalent to EPTC, 2 is 6 to 16 cm, 3 is 17 to 27 cm, 4 is 28 to 38 cm, and 5 is 39 cm or taller. These numbers are given in their respective order. A rating of 5-0-5 means that five plants emerged, none was distorted and the height was over 39 cm. The same procedure may be repeated with lower rates of the test chemical.

Results of tests carried out by this procedure are summarized in the following table.

Evaluation of Amides as EPTC Antidote
(Ratings: emergence-abnormality-plant height)

| ACYL GROUP | | AMINE | | |
|---|---|---|---|---|
| | | Methyl-amine | Benzyl-amine | Cyclohexane-methylamine |
| Dichloroacetyl | 3% | | 5-0-4 | 5-0-5 |
| | ½% | | 5-0-5 | 5-0-5 |
| Trichloroacetyl | 3% | | | |
| | ½% | | | |
| 2-Chloro propionyl | 3% | 5-0-5 | | |
| | ½% | 5-0-5 | | |
| Dibromoacetyl | 3% | 2-0-1 | | 5-0-5 |
| | ½% | 5-0-5 | | 5-2-5 |
| 2-Bromo-butyryl | 3% | 1-0-4 | | |
| | ½% | 5-0-5 | | |
| 2-Bromoiso-butyryl | 3% | | | |
| | ½% | | | |
| 2-Chloro-2-phenyl-acetyl | 3% | | | |
| | ½% | | | |
| Gamma Chloro-n-butyryl | 3% | | | |
| | ½% | | | |
| 3-Chloro-propionyl | 3% | | | |
| | ½% | | | |
| 2-Bromo-propionyl | 3% | | | |
| | ½% | | | |
| 3-Bromo-propionyl | ½ | | | |

| | | p-Methoxy-benzyl-amine | 2-Chloro-benzyl-amine | 3-Chloro-benzyl-amine |
|---|---|---|---|---|
| Dichloroacetyl | 3% | 5-0-5 | 5-0-3 | 3-0-3 |
| | ½% | 5-0-5 | 5-0-5 | 5-0-5 |

-continued

Evaluation of Amides as EPTC Antidote
(Ratings: emergence-abnormality-plant height)

| ACYL GROUP | | AMINE | | |
|---|---|---|---|---|
| Trichloroacetyl | 3% | | | 0-0-0 |
|  | ½% | | | 5-0-5 |
| 2-Chloro propionyl | 3% | | | |
|  | ½% | | | |
| Dibromoacetyl | 3% | | | 3-0-3 |
|  | ½% | | | 5-0-5 |
| 2-Bromo-butyryl | 3% | | 4-0-5 | 2-0-5 |
|  | ½% | | 5-0-5 | 5-0-5 |
| 2-Bromoiso-butyryl | 3% | | | |
|  | ½% | | | |
| 2-Chloro-2-phenyl-acetyl | 3% | | 5-1-5 | |
|  | ½% | | 5-0-5 | |
| Gamma Chloro-n-butryl | 3% | 2-0-5 | 3-0-3 | |
|  | ½% | 5-0-5 | 5-0-5 | |
| 3-Chloro-propionyl | 3% | | | |
|  | ½% | | | |
| 2-Bromo-propionyl | 3% | | | |
|  | ½% | | | |
| 3-Bromo-propionyl | 3% | | | |
|  | ½% | | | |

| | | 4-Chloro-benzyl-amine | 3-Methyl-benzyl-amine | 4-Methyl-benzyl-amine |
|---|---|---|---|---|
| Dichloroacetyl | 3% | 4-0-4 | 5-0-4 | 5-0-5 |
|  | ½% | 4-0-5 | 5-0-4 | 5-0-5 |
| Trichloroacetyl | 3% | 5-0-3 | | |
|  | ½% | 4-0-5 | | |
| 2-Chloro propionyl | 3% | | | |
|  | ½% | | | |
| Dibromoacetyl | 3% | 5-0-5 | | |
|  | ½% | 5-0-5 | | |
| 2-Bromo-butyryl | 3% | 4-0-5 | | |
|  | ½% | 5-0-5 | | |
| 2-Bromoiso-butyryl | 3% | | | |
|  | ½% | | | |
| 2-Chloro-2-phenyl-acetyl | 3% | | | |
|  | ½% | | | |
| Gamma Chloro-n-butryl | 3% | | | 4-0-4 |
|  | ½% | | | 5-0-5 |
| 3-Chloro-propionyl | 3% | | | |
|  | ½% | | | |
| 2-Bromo-propionyl | 3% | | | |
|  | ½% | | | |
| 3-Bromo-propionyl | 3% | | | |
|  | ½% | | | |

| | | 2,4-Dichloro-benzyl amine | 3,4-Dichloro-benzyl amine | 2,4-Dimethyl benzylamine |
|---|---|---|---|---|
| Dichloroacetyl | 3% | 5-0-5 | 5-0-5 | 5-0-5 |
|  | ½% | 5-0-5 | 5-0-5 | 5-0-5 |
| Trichloroacetyl | 3% | | | |
|  | ½% | | | |
| 2-Chloro propionyl | 3% | | | |
|  | ½% | | | |
| Dibromoacetyl | 3% | 5-0-4 | 5-0-5 | |
|  | ½% | 5-0-5 | 5-0-5 | |
| 2-Bromo-butyryl | 3% | 5-0-5 | | |
|  | ½% | 5-1-5 | | |
| 2-Bromoiso-butyryl | 3% | | | |
|  | ½% | | | |
| 2-Chloro-2-phenyl-acetyl | 3% | | | |
|  | ½% | | | |
| Gamma Chloro-n-butryl | 3% | | | 5-0-5 |
|  | ½% | | | 5-3-4 |
| 3-Chloro-propionyl | 3% | | | |
|  | ½% | | | |
| 2-Bromo-propionyl | 3% | | | |
|  | ½% | | | |
| 3-Bromo-propionyl | 3% | | | |
|  | ½% | | | |

| | | 2,5-Dimethyl-benzylamine | dl-α-Methyl benzylamine | p-Chloro-α-methylbenzyl amine |
|---|---|---|---|---|
| Dichloroacetyl | 3% | 5-0-5 | 5-0-5 | 4-0-4 |
|  | ½% | 5-0-5 | 5-0-5 | 5-0-5 |
| Trichloroacetyl | 3% | | | |
|  | ½% | | | |
| 2-Chloro propionyl | 3% | | | |
|  | ½% | | | |
| Dibromoacetyl | 3% | | 5-0-3 | |
|  | ½% | | 5-0-5 | |
| 2-Bromo- | 3% | | | |

-continued

Evaluation of Amides as EPTC Antidote
(Ratings: emergence-abnormality-plant height)

| ACYL GROUP | | AMINE |
|---|---|---|
| butyryl | ½% | |
| 2-Bromoiso-butyryl | 3% | |
|  | ½% | |
| 2-Chloro-2-phenyl-acetyl | 3% | |
|  | ½% | |
| Gamma Chloro-n-butryl | 3% | |
|  | ½% | |
| 3-Chloro-propionyl | 3% | |
|  | ½% | |
| 2-Bromo-propionyl | 3% | |
|  | ½% | |
| 3-Bromo-propionyl | 3% | |
|  | ½% | |

| | | Amino-diphenyl-methane | Ethyl-amine | Ethanol-amine |
|---|---|---|---|---|
| Dichloroacetyl | 3% | 5-0-5 | 4-0-4 | 5-0-5 |
|  | ½% | 5-0-5 | 5-0-5 | 5-0-5 |
| Trichloroacetyl | 3% | | | |
|  | ½% | | | |
| 2-Chloro propionyl | 3% | | | 4-0-5 |
|  | ½% | | | 5-0-5 |
| Dibromoacetyl | 3% | | | |
|  | ½% | | | |
| 2-Bromo-butyryl | 3% | | | |
|  | ½% | | | |
| 2-Bromoiso-butyryl | 3% | | | |
|  | ½% | | | |
| 2-Chloro-2-phenyl-acetyl | 3% | | | |
|  | ½% | | | |
| Gamma Chloro-n-butryl | 3% | | | |
|  | ½% | | | |
| 3-Chloro-propionyl | 3% | | | |
|  | ½% | | | |
| 2-Bromo-propionyl | 3% | | | |
|  | ½% | | | |
| 3-Bromo-propionyl | 3% | | | |
|  | ½% | | | |

| | | Phenethyl-amine | 2-(p-Tolyl)-ethylamine | 2-(p-Chloro-phenyl)ethyl-amine |
|---|---|---|---|---|
| Dichloroacetyl | 3% | 3-0-3 | 5-0-5 | 4-0-5 |
|  | ½% | 5-0-5 | 5-0-5 | 5-0-5 |
| Trichloroacetyl | 3% | | | |
|  | ½% | | | |
| 2-Chloro propionyl | 3% | | | |
|  | ½% | | | |
| Dibromoacetyl | 3% | | | |
|  | ½% | | | |
| 2-Bromo-butyryl | 3% | | | |
|  | ½% | | | |
| 2-Bromoiso-butyryl | 3% | | | |
|  | ½% | | | |
| 2-Chloro-2-phenyl-acetyl | 3% | | | |
|  | ½% | | | |
| Gamma Chloro-n-butryl | 3% | | | |
|  | ½% | | | |
| 3-Chloro-propionyl | 3% | | | |
|  | ½% | | | |
| 2-Bromo-propionyl | 3% | | | |
|  | ½% | | | |
| 3-Bromo-propionyl | 3% | | | |
|  | ½% | | | |

| | | d-α-(1-Naph-thyl)-ethyla-mine | l-α-(1-Naph-thyl)-ethyla-mine |
|---|---|---|---|
| Dichloroacetyl | 3% | 5-0-5 | 4-0-5 |
|  | ½% | 5-0-5 | 5-0-5 |
| Trichloroacetyl | 3% | | |
|  | ½% | | |
| 2-Chloro propionyl | 3% | | 5-0-4 |
|  | ½% | | 5-0-4 |
| Dibromoacetyl | 3% | 5-0-5 | 5-0-4 |
|  | ½% | 5-1-5 | 5-0-5 |
| 2-Bromo-butyryl | 3% | | |
|  | ½% | | |
| 2-Bromoiso-butyryl | 3% | | |
|  | ½% | | |
| 2-Chloro-2-phenyl-acetyl | 3% | | |
|  | ½% | | |
| Gamma Chloro- | 3% | | |

-continued
Evaluation of Amides as EPTC Antidote
(Ratings: emergence-abnormality-plant height)

| ACYL GROUP | | | | |
|---|---|---|---|---|
| n-butryl | ½% | | | |
| 3-Chloro-propionyl | 3% | | | |
| 2-Bromo-propionyl | ½% | | | |
| | 3% | | | |
| 3-Bromo-propionyl | ½% | | | |
| | 3% | | | |
| | ½% | | | |

| ACYL GROUP | | 1,3-Diphenyl-ethylamine | Isopropyl-amine | Allyl-amine |
|---|---|---|---|---|
| Dichloroacetyl | 3% | | 5-0-3 | 5-0-5 |
| | ½% | | 5-0-3 | 3-1-4 |
| Trichloroacetyl | 3% | | | |
| | ½% | | | |
| 2-Chloro propionyl | 3% | | 2-0-3 | |
| | ½% | | 5-0-5 | |
| Dibromoacetyl | 3% | 5-0-5 | | |
| | ½% | 5-0-5 | | |
| 2-Bromo-butyryl | 3% | | | |
| | ½% | | | |
| 2-Bromoiso-butyryl | 3% | | | |
| | ½% | | | |
| 2-Chloro-2-phenyl-acetyl | 3% | | | |
| | ½% | | | |
| Gamma Chloro-n-butryl | 3% | | | |
| | ½% | | | |
| 3-Chloro-propionyl | 3% | | | |
| | ½% | | | |
| 2-Bromo-propionyl | 3% | | | |
| | ½% | | | |
| 3-Bromo-propionyl | 3% | | | |
| | ½% | | | |

| ACYL GROUP | | Propargyl-amine | 2-Amino-1-methoxy-propane | 3-Isopropoxy-propylamine |
|---|---|---|---|---|
| Dichloroacetyl | 3% | | 3-0-3 | 5-0-5 |
| | ½% | | 5-0-5 | 5-0-5 |
| Trichloroacetyl | 3% | | | |
| | ½% | | | |
| 2-Chloro propionyl | 3% | | 5-0-4 | |
| | ½% | | 5-0-5 | |
| Dibromoacetyl | 3% | | | |
| | ½% | | | |
| 2-Bromo-butyryl | 3% | | | |
| | ½% | | | |
| 2-Bromoiso-butyryl | 3% | | | |
| | ½% | | | |
| 2-Chloro-2-phenyl-acetyl | 3% | | | |
| | ½% | | | |
| Gamma Chloro-n-butryl | 3% | | | |
| | ½% | | | |
| 3-Chloro-propionyl | 3% | 5-0-5 | | |
| | ½% | 5-0-5 | | |
| 2-Bromo-propionyl | 3% | | | |
| | ½% | | | |
| 3-Bromo-propionyl | 3% | | | |
| | ½% | | | |

| ACYL GROUP | | Dimethyl-amino-propylamine | 3-Dimethyl-amino-propylamine | Isobutyl-amine |
|---|---|---|---|---|
| Dichloroacetyl | 3% | 5-0-5 | | |
| | ½% | 5-0-5 | | |
| Trichloroacetyl | 3% | | 5-0-5 | 5-0-3 |
| | ½% | | 5-4-4 | 5-0-5 |
| 2-Chloro propionyl | 3% | | | |
| | ½% | | | |
| Dibromoacetyl | 3% | | 5-0-5 | |
| | ½% | | 3-0-5 | |
| 2-Bromo-butyryl | 3% | | | |
| | ½% | | | |
| 2-Bromoiso-butyryl | 3% | | | |
| | ½% | | | |
| 2-Chloro-2-phenyl-acetyl | 3% | | | |
| | ½% | | | |
| Gamma Chloro-n-butryl | 3% | | | |
| | ½% | | | |
| 3-Chloro-propionyl | 3% | | | 1-0-4 |
| | ½% | | | 5-0-5 |
| 2-Bromo-propionyl | 3% | | | |
| | ½% | | | |
| 3-Bromo-propionyl | 3% | | | |
| | ½% | | | |

-continued
Evaluation of Amides as EPTC Antidote
(Ratings: emergence-abnormality-plant height)

| ACYL GROUP | | t-Butyl amine | 2-Amino-1-butanol | 4-Phenyl-butylamine |
|---|---|---|---|---|
| Dichloroacetyl | 3% | 5-0-5 | 5-0-4 | |
| | ½% | 5-0-5 | 5-0-4 | |
| Trichloroacetyl | 3% | | | |
| | ½% | | | |
| 2-Chloro propionyl | 3% | 5-0-5 | | |
| | ½% | 5-0-5 | | |
| Dibromoacetyl | 3% | | | |
| | ½% | | | |
| 2-Bromo-butyryl | 3% | | 1-0-5 | |
| | ½% | | 5-0-5 | |
| 2-Bromoiso-butyryl | 3% | | | |
| | ½% | | | |
| 2-Chloro-2-phenyl-acetyl | 3% | | | |
| | ½% | | | |
| Gamma Chloro-n-butryl | 3% | | | 0-0-0 |
| | ½% | | | 5-0-5 |
| 3-Chloro-propionyl | 3% | | | |
| | ½% | | | |
| 2-Bromo-propionyl | 3% | | | |
| | ½% | | | |
| 3-Bromo-propionyl | 3% | | | |
| | ½% | | | |

| ACYL GROUP | | α,α-Dimethyl-phenethyl-amine | t-Pentyl amine | 2-Amino-3,3-dimethyl-butane |
|---|---|---|---|---|
| Dichloroacetyl | 3% | 4-0-5 | | 5-0-4 |
| | ½% | 5-0-5 | | 5-0-4 |
| Trichloroacetyl | 3% | | | 4-0-2 |
| | ½% | | | 5-0-5 |
| 2-Chloro propionyl | 3% | | 0-0-0 | 3-0-4 |
| | ½% | | 5-0-5 | 5-0-5 |
| Dibromoacetyl | 3% | | | 2-0-3 |
| | ½% | | | 5-0-5 |
| 2-Bromo-butyryl | 3% | | | |
| | ½% | | | |
| 2-Bromoiso-butyryl | 3% | | | |
| | ½% | | | |
| 2-Chloro-2-phenyl-acetyl | 3% | | | |
| | ½% | | | |
| Gamma Chloro-n-butryl | 3% | | | |
| | ½% | | | |
| 3-Chloro-propionyl | 3% | | | |
| | ½% | | | |
| 2-Bromo-propionyl | 3% | | 5-0-5 | |
| | ½% | | 5-0-5 | |
| 3-Bromo-propionyl | 3% | | | |
| | ½% | | | |

| ACYL GROUP | | 2-Amino heptane | 2-Ethylhexyl-amine | t-Octyl-amine |
|---|---|---|---|---|
| Dichloroacetyl | 3% | 5-0-4 | 1-0-4 | |
| | ½% | 5-0-5 | 5-0-5 | |
| Trichloroacetyl | 3% | | | |
| | ½% | | | |
| 2-Chloro propionyl | 3% | | | |
| | ½% | | | |
| Dibromoacetyl | 3% | | | 3-0-5 |
| | ½% | | | 5-0-5 |
| 2-Bromo-butyryl | 3% | | | |
| | ½% | | | |
| 2-Bromoiso-butyryl | 3% | | | |
| | ½% | | | |
| 2-Chloro-2-phenyl-acetyl | 3% | | | |
| | ½% | | | |
| Gamma Chloro-n-butryl | 3% | | | |
| | ½% | | | |
| 3-Chloro-propionyl | 3% | | | 5-0-5 |
| | ½% | | | 5-1-5 |
| 2-Bromo-propionyl | 3% | | | |
| | ½% | | | |
| 3-Bromo-propionyl | 3% | | | |
| | ½% | | | |

| ACYL GROUP | | T-Tetra-decyl-amine | Cyclo-propyl-amine | Cyclo-butyl-amine |
|---|---|---|---|---|
| Dichloroacetyl | 3% | | 5-0-2 | |
| | ½% | | 5-0-4 | |
| Trichloroacetyl | 3% | | | |

Evaluation of Amides as EPTC Antidote
(Ratings: emergence-abnormality-plant height)

| ACYL GROUP | | AMINE | | |
|---|---|---|---|---|
| 2-Chloro propionyl | 3% ½% | | | 3-0-1 5-0-5 |
| Dibromoacetyl | 3% ½% | 4-0-5 5-0-5 | | |
| 2-Bromo-butyryl | 3% ½% | | | |
| 2-Bromoiso-butyryl | 3% ½% | | | |
| 2-Chloro-2-phenyl-acetyl | 3% ½% | | | |
| Gamma Chloro-n-butryl | 3% ½% | 2-0-5 5-0-5 | | |
| 3-Chloro-propionyl | 3% ½% | | | |
| 2-Bromo-propionyl | 3% ½% | | | |
| 3-Bromo-propionyl | 3% ½% | | | |

| | | Cyclo-heptyl-amine | Cyclo-octyl-amine | 1-Adamantan-amine |
|---|---|---|---|---|
| Dichloroacetyl | 3% ½% | 3-0-5 5-0-5 | | 5-0-5 5-0-4 |
| Trichloroacetyl | 3% ½% | 0-0-0 5-0-5 | | |
| 2-Chloro propionyl | 3% ½% | | 5-0-3 5-0-4 | |
| Dibromoacetyl | 3% ½% | 3-0-5 3-0-5 | 4-2-5 5-0-5 | |
| 2-Bromo-butyryl | 3% ½% | | 3-0-5 5-0-5 | |
| 2-Bromoiso-butyryl | 3% ½% | | | |
| 2-Chloro-2-phenyl-acetyl | 3% ½% | | | |
| Gamma Chloro-n-butryl | 3% ½% | | | |
| 3-Chloro-propionyl | 3% ½% | | | |
| 2-Bromo-propionyl | 3% ½% | | | |
| 3-Bromo-propionyl | 3% ½% | | | |

| | | Hepta-methylene-imine | 1-Naphthyl-amine | 1-Amino-5,6,7,9-tetrahydro-naphthalene |
|---|---|---|---|---|
| Dichloroacetyl | 3% ½% | 5-0-4 4-0-5 | 5-0-5 5-0-5 | 5-0-4 5-0-5 |
| Trichloroacetyl | 3% ½% | 0-0-0 5-0-5 | | 5-5-1 5-0-5 |
| 2-Chloro propionyl | 3% ½% | | 5-0-3 5-0-5 | |
| Dibromoacetyl | 3% ½% | | | |
| 2-Bromo-butyryl | 3% ½% | | | |
| 2-Bromoiso-butyryl | 3% ½% | | | |
| 2-Chloro-2-phenyl-acetyl | 3% ½% | | 5-0-5 5-0-5 | |
| Gamma Chloro-n-butryl | 3% ½% | | | |
| 3-Chloro-propionyl | 3% ½% | | | |
| 2-Bromo-propionyl | 3% ½% | | | |
| 3-Bromo-propionyl | 3% ½% | | | |

| | | 2-Fluoro-aniline | α-Chloro-aniline | p-Chloro-aniline |
|---|---|---|---|---|
| Dichloroacetyl | 3% ½% | | | 2-2-1 5-0-3 |
| Trichloroacetyl | 3% ½% | | | 0-0-0 0-0-0 |
| 2-Chloro propionyl | 3% ½% | | 0-0-0 4-0-3 | 0-0-0 4-0-2 |
| Dibromoacetyl | 3% ½% | | | 1-0-1 5-0-5 |
| 2-Bromo-butyryl | 3% ½% | | | |

Evaluation of Amides as EPTC Antidote
(Ratings: emergence-abnormality-plant height)

| ACYL GROUP | | AMINE | | |
|---|---|---|---|---|
| 2-Bromoiso-butyryl | 3% ½% | | | |
| 2-Chloro-2-phenyl-acetyl | 3% ½% | | | 4-0-2 4-0-5 |
| Gamma Chloro-n-butyryl | 3% ½% | 5-0-5 5-0-5 | | 0-0-0 5-0-4 |
| 3-Chloro-propionyl | 3% ½% | | | |
| 2-Bromo-propionyl | 3% ½% | | | |
| 3-Bromo-propionyl | 3% ½% | | | |

| | | 3-Chloro-aniline | 2,6-Dichloro-aniline | p-Bromo-aniline |
|---|---|---|---|---|
| Dichloroacetyl | 3% ½% | | 5-0-5 5-0-5 | 0-0-0 5-0-5 |
| Trichloroacetyl | 3% ½% | | | 5-5-1 5-5-1 |
| 2-Chloro propionyl | 3% ½% | 0-0-0 4-0-2 | 3-3-2 5-0-5 | 0-0-0 5-5-1 |
| Dibromoacetyl | 3% ½% | | | 3-0-2 5-0-5 |
| 2-Bromo-butyryl | 3% ½% | | | |
| 2-Bromoiso-butyryl | 3% ½% | | | |
| 2-Chloro-2-phenyl-acetyl | 3% ½% | | | |
| Gamma Chloro-n-butyryl | 3% ½% | | | |
| 3-Chloro-propionyl | 3% ½% | | | |
| 2-Bromo-propionyl | 3% ½% | | | 4-4-1 5-5-1 |
| 3-Bromo-propionyl | 3% ½% | | | 5-5-2 5-5-1 |

| | | o-Toluidine | m-Toluidine | 2,6-Dimethyl-aniline |
|---|---|---|---|---|
| Dichloroacetyl | 3% ½% | 5-0-5 5-0-5 | | 5-0-5 5-2-5 |
| Trichloroacetyl | 3% ½% | | | |
| 2-Chloro propionyl | 3% ½% | 3-0-3 5-0-5 | | |
| Dibromoacetyl | 3% ½% | | 2-0-3 5-0-5 | 5-0-5 5-0-4 |
| 2-Bromo-butyryl | 3% ½% | 1-0-5 5-0-5 | | |
| 2-Bromoiso-butyryl | 3% ½% | | | |
| 2-Chloro-2-phenyl-acetyl | 3% ½% | | | |
| Gamma Chloro-n-butyryl | 3% ½% | | | |
| 3-Chloro-propionyl | 3% ½% | | | |
| 2-Bromo-propionyl | 3% ½% | | | |
| 3-Bromo-propionyl | 3% ½% | | | |

| | | 2,4,5-Tri-methyl-aniline | 2,4,6-Tri-methyl-aniline | 2-Ethyl-aniline |
|---|---|---|---|---|
| Dichloroacetyl | 3% ½% | 4-0-5 5-0-5 | | |
| Trichloroacetyl | 3% ½% | | | |
| 2-Chloro propionyl | 3% ½% | | | |
| Dibromoacetyl | 3% ½% | | 3-0-1 5-0-5 | |
| 2-Bromo-butyryl | 3% ½% | | 3-0-4 5-0-5 | |
| 2-Bromoiso-butyryl | 3% ½% | | | |
| 2-Chloro-2-phenyl-acetyl | 3% ½% | | | |
| Gamma Chloro-n-butyryl | 3% ½% | | | 1-0-5 5-0-5 |
| 3-Chloro-propionyl | 3% ½% | | | |

-continued
Evaluation of Amides as EPTC Antidote
(Ratings: emergence-abnormality-plant height)

| ACYL GROUP | | AMINE | | |
|---|---|---|---|---|
| 2-Bromo-propionyl | 3% | | | |
| | ½% | | | |
| 3-Bromo-propionyl | 3% | | | |
| | ½% | | | |

| ACYL GROUP | | 2-Amino-p-cymene | 2-Chloro-5-methyl-aniline | 4-Chloro-2,5-dimethoxy-aniline |
|---|---|---|---|---|
| Dichloroacetyl | 3% | | 2-0-4 | 5-0-5 |
| | ½% | | 5-0-4 | 5-0-5 |
| Trichloroacetyl | 3% | | | |
| | ½% | | | |
| 2-Chloro propionyl | 3% | | | |
| | ½% | | | |
| Dibromoacetyl | 3% | | 5-0-5 | |
| | ½% | | 5-0-5 | |
| 2-Bromo-butyryl | 3% | | | |
| | ½% | | | |
| 2-Bromoiso-butyryl | 3% | | | |
| | ½% | | | |
| 2-Chloro-2-phenyl-acetyl | 3% | | | |
| | ½% | | | |
| Gamma Chloro-n-butryl | 3% | 4-0-5 | | |
| | ½% | 5-0-5 | | |
| 3-Chloro-propionyl | 3% | | | |
| | ½% | | | |
| 2-Bromo-propionyl | 3% | | | |
| | ½% | | | |
| 3-Bromo-propionyl | 3% | | | |
| | ½% | | | |

| ACYL GROUP | | 2-Amino-thiophenyl | 3-Amino-thiophenyl | m-Amino-phenol |
|---|---|---|---|---|
| Dichloroacetyl | 3% | 5-0-5 | 4-0-5 | 3-0-3 |
| | ½% | 5-4-4 | 5-0-5 | 5-0-5 |
| Trichloroacetyl | 3% | | | |
| | ½% | | | |
| 2-Chloro propionyl | 3% | | | |
| | ½% | | | |
| Dibromoacetyl | 3% | | | |
| | ½% | | | |
| 2-Bromo-butyryl | 3% | | | |
| | ½% | | | |
| 2-Bromoiso-butyryl | 3% | | | |
| | ½% | | | |
| 2-Chloro-2-phenyl-acetyl | 3% | | | |
| | ½% | | | |
| Gamma Chloro-n-butryl | 3% | 5-0-5 | 3-0-5 | |
| | ½% | 5-3-3 | 5-0-5 | |
| 3-Chloro-propionyl | 3% | | | |
| | ½% | | | |
| 2-Bromo-propionyl | 3% | | | |
| | ½% | | | |
| 3-Bromo-propionyl | 3% | | | |
| | ½% | | | |

| ACYL GROUP | | o-Amino-benzyl Alcohol | 3-Chloro-4-methoxy aniline | 2,5-Di-methoxy-aniline |
|---|---|---|---|---|
| Dichloroacetyl | 3% | 4-0-2 | 5-0-4 | 4-0-4 |
| | ½% | 5-0-5 | 5-0-5 | 5-0-5 |
| Trichloroacetyl | 3% | | | |
| | ½% | | | |
| 2-Chloro propionyl | 3% | | | |
| | ½% | | | |
| Dibromoacetyl | 3% | | | 5-0-5 |
| | ½% | | | 3-0-5 |
| 2-Bromo-butyryl | 3% | | | |
| | ½% | | | |
| 2-Bromoiso-butyryl | 3% | | | |
| | ½% | | | |
| 2-Chloro-2-phenyl-acetyl | 3% | | | |
| | ½% | | | |
| Gamma Chloro-n-butryl | 3% | 3-0-4 | 3-0-1 | |
| | ½% | 5-0-5 | 5-0-5 | |
| 3-Chloro-propionyl | 3% | | | |
| | ½% | | | |
| 2-Bromo-propionyl | 3% | | | |
| | ½% | | | |
| 3-Bromo-propionyl | 3% | | | |
| | ½% | | | |

| ACYL GROUP | | 2-Methoxy-5-methylaniline | 4-Methoxy-2-methylaniline | 4-Aminophenyl-ether |
|---|---|---|---|---|
| Dichloroacetyl | 3% | 5-0-5 | 5-0-4 | 5-0-5 |
| | ½% | 5-0-4 | 5-0-4 | 5-0-5 |
| Trichloroacetyl | 3% | | | |
| | ½% | | | |
| 2-Chloro propionyl | 3% | | | |
| | ½% | | | |
| Dibromoacetyl | 3% | | 5-0-5 | |
| | ½% | | 4-2-4 | |
| 2-Bromo-butyryl | 3% | | | |
| | ½% | | | |
| 2-Bromoiso-butyryl | 3% | | | |
| | ½% | | | |
| 2-Chloro-2-phenyl-acetyl | 3% | | | |
| | ½% | | | |
| Gamma Chloro-n-butryl | 3% | | | |
| | ½% | | | |
| 3-Chloro-propionyl | 3% | | | |
| | ½% | | | |
| 2-Bromo-propionyl | 3% | | | |
| | ½% | | | |
| 3-Bromo-propionyl | 3% | | | |
| | ½% | | | |

| ACYL GROUP | | 2-Amino-4-chlorophenyl ether | o-(2,4-Di-chloro-phenoxy) aniline | p-Amino-aceto-phenone |
|---|---|---|---|---|
| Dichloroacetyl | 3% | 5-0-4 | 5-0-5 | |
| | ½% | 5-0-5 | 5-1-5 | |
| Trichloroacetyl | 3% | | | |
| | ½% | | | |
| 2-Chloro propionyl | 3% | | | |
| | ½% | | | |
| Dibromoacetyl | 3% | | | |
| | ½% | | | |
| 2-Bromo-butyryl | 3% | | | |
| | ½% | | | |
| 2-Bromoiso-butyryl | 3% | | | |
| | ½% | | | |
| 2-Chloro-2-phenyl-acetyl | 3% | | | |
| | ½% | | | 0-0-0 |
| Gamma Chloro-n-butryl | 3% | | | 5-0-5 |
| | ½% | | | |
| 3-Chloro-propionyl | 3% | | | |
| | ½% | | | |
| 2-Bromo-propionyl | 3% | | | |
| | ½% | | | |
| 3-Bromo-propionyl | 3% | | | |
| | ½% | | | |

| ACYL GROUP | | 2-Methyl-4-nitro-aniline | 2-Methyl-6-nitro-aniline | 4-Methyl-2-nitro-aniline |
|---|---|---|---|---|
| Dichloroacetyl | 3% | 5-0-5 | | |
| | ½% | 4-0-5 | | |
| Trichloroacetyl | 3% | | | |
| | ½% | | | |
| 2-Chloro propionyl | 3% | | | |
| | ½% | | | |
| Dibromoacetyl | 3% | | | |
| | ½% | | | |
| 2-Bromo-butyryl | 3% | | | |
| | ½% | | | |
| 2-Bromoiso-butyryl | 3% | | | |
| | ½% | | | |
| 2-Chloro-2-phenyl-acetyl | 3% | | 0-0-0 | 0-0-0 |
| | ½% | | | |
| Gamma Chloro-n-butryl | 3% | | 5-0-5 | 5-0-5 |
| | ½% | | | |
| 3-Chloro-propionyl | 3% | | | |
| | ½% | | | |
| 2-Bromo-propionyl | 3% | | | |
| | ½% | | | |
| 3-Bromo-propionyl | 3% | | | |
| | ½% | | | |

| ACYL GROUP | | 2-Methoxy-4-nitro-aniline | 2-Methoxy-5-nitro-aniline | 4-Methoxy-2-nitro-aniline |
|---|---|---|---|---|
| Dichloroacetyl | 3% | 5-0-5 | 5-0-5 | |
| | ½% | 5-0-5 | 5-0-4 | |
| Trichloroacetyl | 3% | | | |

Evaluation of Amides as EPTC Antidote
(Ratings: emergence-abnormality-plant height)

| ACYL GROUP | | AMINE | | |
|---|---|---|---|---|
| 2-Chloro propionyl | 3% ½% | | | |
| Dibromoacetyl | 3% ½% | | | |
| 2-Bromo-butyryl | 3% ½% | | | |
| 2-Bromoiso-butyryl | 3% ½% | | | |
| 2-Chloro-2-phenyl-acetyl | 3% ½% | | | |
| Gamma Chloro-n-butryl | 3% ½% | 3-0-3 5-0-5 | | |
| 3-Chloro-propionyl | 3% ½% | | | |
| 2-Bromo-propionyl | 3% ½% | | | |
| 3-Bromo-propionyl | 3% ½% | | | |

| | | Dimethyl-amine | Diethyl-amine | Diisopropyl-amine |
|---|---|---|---|---|
| Dichloroacetyl | 3% ½% | 5-0-5 5-0-5 | 2-0-3 5-0-5 | 3-0-4 5-0-5 |
| Trichloroacetyl | 3% ½% | | | |
| 2-Chloro propionyl | 3% ½% | | | |
| Dibromoacetyl | 3% ½% | | | |
| 2-Bromo-butyryl | 3% ½% | | | |
| 2-Bromoiso-butyryl | 3% ½% | | | |
| 2-Chloro-2-phenyl-acetyl | 3% ½% | | | |
| Gamma Chloro-n-butryl | 3% ½% | | | |
| 3-Chloro-propionyl | 3% ½% | | | |
| 2-Bromo-propionyl | 3% ½% | | | |
| 3-Bromo-propionyl | 3% ½% | | | |

| | | Diallyl-amine | Dipropargyl-amine | Di-n-Butyl-amine |
|---|---|---|---|---|
| Dichloroacetyl | 3% ½% | 0-0-0 5-0-5 | | 0-0-0 5-0-5 |
| Trichloroacetyl | 3% ½% | | | |
| 2-Chloro propionyl | 3% ½% | | | |
| Dibromoacetyl | 3% ½% | | | |
| 2-Bromo-butyryl | 3% ½% | | 0-0-0 5-0-5 | |
| 2-Bromoiso-butyryl | 3% ½% | | | |
| 2-Chloro-2-phenyl-acetyl | 3% ½% | | | |
| Gamma Chloro-n-butryl | 3% ½% | | 4-0-5 5-0-5 | |
| 3-Chloro-propionyl | 3% ½% | | | |
| 2-Bromo-propionyl | 3% ½% | | 0-0-0 5-0-5 | |
| 3-Bromo-propionyl | 3% ½% | | | |

| | | Diisobutyl-amine | Diisopentyl-amine | Di-n-octyl-amine |
|---|---|---|---|---|
| Dichloroacetyl | 3% ½% | 5-0-5 5-1-4 | | 5-0-5 5-3-3 |
| Trichloroacetyl | 3% ½% | | | |
| 2-Chloro propionyl | 3% ½% | | | |
| Dibromoacetyl | 3% ½% | | | |
| 2-Bromo-butyryl | 3% ½% | | | |
| 2-Bromoiso-butyryl | 3% ½% | | | |
| 2-Chloro-2- | 3% | | 5-0-5 | |

Evaluation of Amides as EPTC Antidote
(Ratings: emergence-abnormality-plant height)

| ACYL GROUP | | AMINE | | |
|---|---|---|---|---|
| phenyl-acetyl | ½% | 5-1-5 | | |
| Gamma Chloro-n-butryl | 3% ½% | | | |
| 3-Chloro-propionyl | 3% ½% | | | |
| 2-Bromo-propionyl | 3% ½% | | | |
| 3-Bromo-propionyl | 3% ½% | | | |

| | | N-methyl-butylamine | N-methyl-ethanolamine | N-methyl-phenethylamine |
|---|---|---|---|---|
| Dichloroacetyl | 3% ½% | 1-0-4 5-0-4 | | 2-0-4 5-0-5 |
| Trichloroacetyl | 3% ½% | | | |
| 2-Chloro propionyl | 3% ½% | | 5-0-5 5-0-5 | |
| Dibromoacetyl | 3% ½% | 1-0-4 5-0-5 | | |
| 2-Bromo-butyryl | 3% ½% | | | |
| 2-Bromoiso-butyryl | 3% ½% | | | |
| 2-Chloro-2-phenyl-acetyl | 3% ½% | | | |
| Gamma Chloro-n-butryl | 3% ½% | | | |
| 3-Chloro-propionyl | 3% ½% | | | |
| 2-Bromo-propionyl | 3% ½% | | | |
| 3-Bromo-propionyl | 3% ½% | | | |

| | | o-Chloro-N-methylbenzyl-amine | N-Benzyl-methyl-amine | N-Methyl-methyl anthranilate |
|---|---|---|---|---|
| Dichloroacetyl | 3% ½% | | | 5-0-3 5-0-3 |
| Trichloroacetyl | 3% ½% | 3-0-5 5-0-5 | 2-0-4 5-0-5 | |
| 2-Chloro propionyl | 3% ½% | | | 0-0-0 5-0-5 |
| Dibromoacetyl | 3% ½% | | | |
| 2-Bromo-butyryl | 3% ½% | | | |
| 2-Bromoiso-butyryl | 3% ½% | | | |
| 2-Chloro-2-phenyl-acetyl | 3% ½% | 5-0-5 5-2-4 | 5-0-5 4-0-4 | |
| Gamma Chloro-n-butryl | 3% ½% | | | |
| 3-Chloro-propionyl | 3% ½% | | | |
| 2-Bromo-propionyl | 3% ½% | | | |
| 3-Bromo-propionyl | 3% ½% | | | |

| | | N-Isopropyl-benzylamine | Dibenzyl-amine | N-Ethyl-n-butyl-amine |
|---|---|---|---|---|
| Dichloroacetyl | 3% ½% | | 5-0-5 5-0-5 | 0-0-0 5-0-5 |
| Trichloroacetyl | 3% ½% | 5-5-1 5-0-5 | | |
| 2-Chloro propionyl | 3% ½% | | | |
| Dibromoacetyl | 3% ½% | | 4-0-5 5-0-5 | |
| 2-Bromo-butyryl | 3% ½% | | | |
| 2-Bromoiso-butyryl | 3% ½% | | | |
| 2-Chloro-2-phenyl-acetyl | 3% ½% | | | |
| Gamma Chloro-n-butryl | 3% ½% | | | |
| 3-Chloro-propionyl | 3% ½% | | | |
| 2-Bromo- | 3% | | | |

Evaluation of Amides as EPTC Antidote
(Ratings: emergence-abnormality-plant height)

| ACYL GROUP | | AMINE | | |
|---|---|---|---|---|
| propionyl | ½% | | | |
| 3-Bromo-propionyl | 3% | | | |
| | ½% | | | |

| ACYL GROUP | | N-Ethyl-aniline | N-Ethyl-o-toluidine | N-Ethyl-m-toluidine |
|---|---|---|---|---|
| Dichloroacetyl | 3% | | 2-0-3 | |
| | ½% | | 5-0-5 | |
| Trichloroacetyl | 3% | | | 3-0-2 |
| | ½% | | | 5-0-5 |
| 2-Chloro propionyl | 3% | | | 0-0-0 |
| | ½% | | | 5-0-5 |
| Dibromoacetyl | 3% | | | |
| | ½% | | | |
| 2-Bromo-butyryl | 3% | | | |
| | ½% | | | |
| 2-Bromoiso-butyryl | 3% | | | |
| | ½% | | | |
| 2-Chloro-2-phenyl-acetyl | 3% | | | |
| | ½% | | | |
| Gamma Chloro-n-butryl | 3% | 0-0-0 | | |
| | ½% | 5-0-5 | | |
| 3-Chloro-propionyl | 3% | | | |
| | ½% | | | |
| 2-Bromo-propionyl | 3% | | | |
| | ½% | | | |
| 3-Bromo-propionyl | 3% | | | |
| | ½% | | | |

| ACYL GROUP | | N-Ethyl-1-naphthyl-amine | N-isopropyl-cyclohexyl-amine | N-Iso-propyl-aniline |
|---|---|---|---|---|
| Dichloroacetyl | 3% | 5-0-4 | | 5-0-5 |
| | ½% | 5-0-5 | | 4-0-5 |
| Trichloroacetyl | 3% | | | |
| | ½% | | | |
| 2-Chloro propionyl | 3% | | 1-0-5 | |
| | ½% | | 5-0-5 | |
| Dibromoacetyl | 3% | | | |
| | ½% | | | |
| 2-Bromo-butyryl | 3% | | | |
| | ½% | | | |
| 2-Bromoiso-butyryl | 3% | | | |
| | ½% | | | |
| 2-Chloro-2-phenyl-acetyl | 3% | | | |
| | ½% | | | |
| Gamma Chloro-n-butryl | 3% | | | |
| | ½% | | | |
| 3-Chloro-propionyl | 3% | | | |
| | ½% | | | |
| 2-Bromo-propionyl | 3% | | | |
| | ½% | | | |
| 3-Bromo-propionyl | 3% | | | |
| | ½% | | | |

| ACYL GROUP | | N-Allyl-cyclohexyl-amine | N-Allyl-o-toluidine | N-(n-Butyl)-benzylamine |
|---|---|---|---|---|
| Dichloroacetyl | 3% | 3-0-5 | | 5-0-5 |
| | ½% | 5-0-5 | | 5-0-5 |
| Trichloroacetyl | 3% | | | |
| | ½% | | | |
| 2-Chloro-propionyl | 3% | | | |
| | ½% | | | |
| Dibromoacetyl | 3% | | | |
| | ½% | | | |
| 2-Bromo-butyryl | 3% | | | |
| | ½% | | | |
| 2-Bromoiso-butyryl | 3% | | | |
| | ½% | | | |
| 2-Chloro-2-phenyl-acetyl | 3% | | | |
| | ½% | | | |
| Gamma Chloro-n-butryl | 3% | | 4-0-4 | |
| | ½% | | 5-0-5 | |
| 3-Chloro-propionyl | 3% | | | |
| | ½% | | | |
| 2-Bromo-propionyl | 3% | | | |
| | ½% | | | |
| 3-Bromo-propionyl | 3% | | | |
| | ½% | | | |

| | | L-(2-Amino-ethyl)- | 3-Amino-N-ethyl- |
|---|---|---|---|

| ACYL GROUP | | piperazine | piperidine | Pyrrolidine |
|---|---|---|---|---|
| Dichloroacetyl | 3% | 5-0-5 | 4-0-5 | |
| | ½% | 5-0-5 | 5-0-5 | |
| Trichloroacetyl | 3% | | | |
| | ½% | | | |
| 2-Chloro propionyl | 3% | | | |
| | ½% | | | |
| Dibromoacetyl | 3% | | | 4-0-4 |
| | ½% | | | 5-0-5 |
| 2-Bromo-butyryl | 3% | | | |
| | ½% | | | |
| 2-Bromoiso-butyryl | 3% | | | |
| | ½% | | | |
| 2-Chloro-2-phenyl-acetyl | 3% | | | |
| | ½% | | | |
| Gamma Chloro-n-butryl | 3% | | | |
| | ½% | | | |
| 3-Chloro-propionyl | 3% | | | |
| | ½% | | | |
| 2-Bromo-propionyl | 3% | | | |
| | ½% | | | |
| 3-Bromo-propionyl | 3% | | | |
| | ½% | | | |

| ACYL GROUP | | 2,5-Dimethyl-pyrrolidine | Pyrrole | 2,5-Dimethyl-pyrrole |
|---|---|---|---|---|
| Dichloroacetyl | 3% | 1-0-1 | 5-0-5 | 5-0-5 |
| | ½% | 5-0-5 | 4-0-5 | 5-0-5 |
| Trichloroacetyl | 3% | | | 4-4-1 |
| | ½% | | | 5-0-5 |
| 2-Chloro propionyl | 3% | | | |
| | ½% | | | |
| Dibromoacetyl | 3% | | 5-0-5 | |
| | ½% | | 5-4-2 | |
| 2-Bromo-butyryl | 3% | | | |
| | ½% | | | |
| 2-Bromoiso-butyryl | 3% | | | |
| | ½% | | | |
| 2-Chloro-2-phenyl-acetyl | 3% | | | |
| | ½% | | | |
| Gamma Chloro-n-butryl | 3% | | | |
| | ½% | | | |
| 3-Chloro-propionyl | 3% | | | |
| | ½% | | | |
| 2-Bromo-propionyl | 3% | | | |
| | ½% | | | |
| 3-Bromo-propionyl | 3% | | | |
| | ½% | | | |

| ACYL GROUP | | Tetrahydro-furyl-amine | N-Methyl-tetrahydro-furfurylamine | Piperidine |
|---|---|---|---|---|
| Dichloroacetyl | 3% | 0-0-0 | 5-0-3 | 0-0-0 |
| | ½% | 5-0-5 | 5-0-5 | 5-0-5 |
| Trichloroacetyl | 3% | | | |
| | ½% | | | |
| 2-Chloro propionyl | 3% | | | |
| | ½% | | | |
| Dibromoacetyl | 3% | 1-0-2 | 1-0-4 | |
| | ½% | 5-0-5 | 5-0-5 | |
| 2-Bromo-butyryl | 3% | | | |
| | ½% | | | |
| 2-Bromoiso-butyryl | 3% | | | |
| | ½% | | | |
| 2-Chloro-2-phenyl-acetyl | 3% | | | |
| | ½% | | | |
| Gamma Chloro-n-butryl | 3% | 5-0-5 | | |
| | ½% | 5-5-2 | | |
| 3-Chloro-propionyl | 3% | | | |
| | ½% | | | |
| 2-Bromo-propionyl | 3% | | | |
| | ½% | | | |
| 3-Bromo-propionyl | 3% | | | |
| | ½% | | | |

| ACYL GROUP | | 4-(Amino-methyl)-piperidine | 2,4,6-Tri-methyl-piperidine | 2,2,6,6-Tetra-methyl piperidine |
|---|---|---|---|---|
| Dichloroacetyl | 3% | 5-0-5 | | |
| | ½% | 5-1-5 | | |
| Trichloroacetyl | 3% | | 5-0-5 | |
| | ½% | | 5-0-5 | |

-continued

Evaluation of Amides as EPTC Antidote
(Ratings: emergence-abnormality-plant height)

| ACYL GROUP | | AMINE | | |
|---|---|---|---|---|
| 2-Chloro propionyl | 3% ½% | | | |
| Dibromoacetyl | 3% ½% | | 4-0-4 5-0-5 | |
| 2-Bromo-butyryl | 3% ½% | | | |
| 2-Bromoiso-butyryl | 3% ½% | | | |
| 2-Chloro-2-phenyl-acetyl | 3% ½% | | | |
| Gamma Chloro-n-butryl | 3% ½% | | | |
| 3-Chloro-propionyl | 3% ½% | | | |
| 2-Bromo-propionyl | 3% ½% | | | |
| 3-Bromo-propionyl | 3% ½% | | | |

| | | 2-Amino-3-picoline | 2-Amino-4-picoline | 2-Amino-5-picoline |
|---|---|---|---|---|
| Dichloroacetyl | 3% ½% | 5-0-5 5-5-1 | 3-0-5 5-0-5 | 3-0-5 5-0-5 |
| Trichloroacetyl | 3% ½% | | | |
| 2-Chloro-propionyl | 3% ½% | | | |
| Dibromoacetyl | 3% ½% | | | |
| 2-Bromo-butyryl | 3% ½% | | | |
| 2-Bromoiso-butyryl | 3% ½% | | | |
| 2-Chloro-2-phenyl-acetyl | 3% ½% | | | |
| Gamma Chloro-n-butryl | 3% ½% | | | |
| 3-Chloro-propionyl | 3% ½% | | | |
| 2-Bromo-propionyl | 3% ½% | | | |
| 3-Bromo-propionyl | 3% ½% | | | |

| | | 2-Amino-6-picoline | 2-Amino-pyridine | 2-Amino-5-Chloro-pyridine |
|---|---|---|---|---|
| Dichloroacetyl | 3% ½% | 5-0-5 4-0-5 | 4-1-3 5-0-5 | 4-0-3 5-0-5 |
| Trichloroacetyl | 3% ½% | | | |
| 2-Chloro propionyl | 3% ½% | | | |
| Dibromoacetyl | 3% ½% | | | 2-0-4 5-0-5 |
| 2-Bromo-butyryl | 3% ½% | | | |
| 2-Bromoiso-butyryl | 3% ½% | | | |
| 2-Chloro-2-phenyl-acetyl | 3% ½% | | | |
| Gamma Chloro-n-butryl | 3% ½% | | 3-0-1 5-0-5 | |
| 3-Chloro-propionyl | 3% ½% | | | |
| 2-Bromo-propionyl | 3% ½% | | | |
| 3-Bromo-propionyl | 3% ½% | | | |

| | | 2-Amino-methyl-pyridine | 3-Amino-methyl-pyridine | 4-Amino-methyl-pyridine |
|---|---|---|---|---|
| Dichloroacetyl | 3% ½% | 2-0-4 5-0-5 | | 5-0-5 5-0-5 |
| Trichloroacetyl | 3% ½% | | | 4-0-5 5-0-5 |
| 2-Chloro propionyl | 3% ½% | | | |
| Dibromoacetyl | 3% ½% | | | |
| 2-Bromo-butyryl | 3% ½% | | | |
| 2-Bromoiso-butyryl | 3% ½% | | | |

-continued

Evaluation of Amides as EPTC Antidote
(Ratings: emergence-abnormality-plant height)

| ACYL GROUP | | AMINE | | |
|---|---|---|---|---|
| 2-Chloro-2-phenyl-acetyl | 3% ½% | | | |
| Gamma Chloro-n-butryl | 3% ½% | 5-0-5 5-0-5 | | |
| 3-Chloro-propionyl | 3% ½% | | | |
| 2-Bromo-propionyl | 3% ½% | | | |
| 3-Bromo-propionyl | 3% ½% | | | |

| | | Morpholine | 2-Amino-4-chlorobenzo-thiazole | 2-Amino-6-chlorobenzo-thiazole |
|---|---|---|---|---|
| Dichloroacetyl | 3% ½% | 2-0-2 5-0-5 | 5-0-5 5-5-2 | 0-0-0 0-0-0 |
| Trichloroacetyl | 3% ½% | | | |
| 2-Chloro propionyl | 3% ½% | | | 4-0-5 5-0-5 |
| Dibromoacetyl | 3% ½% | | | |
| 2-Bromo-butyryl | 3% ½% | | | |
| 2-Bromoiso-butyryl | 3% ½% | | | |
| 2-Chloro-2-phenyl-acetyl | 3% ½% | | | |
| Gamma Chloro-n-butryl | 3% ½% | | | |
| 3-Chloro-propionyl | 3% ½% | | | |
| 2-Bromo-propionyl | 3% ½% | | | |
| 3-Bromo-propionyl | 3% ½% | | | |

| | | Piperonyl-amine | 1,2,3,4-Tetrahydro-quinoline | 4-Amino-quinaldine |
|---|---|---|---|---|
| Dichloroacetyl | 3% ½% | 4-0-5 5-0-5 | | 5-0-5 5-3-3 |
| Trichloroacetyl | 3% ½% | | | |
| 2-Chloro propionyl | 3% ½% | | | |
| Dibromoacetyl | 3% ½% | | | 1-0-4 5-0-5 |
| 2-Bromo-butyryl | 3% ½% | | | |
| 2-Bromoiso-butyryl | 3% ½% | | | |
| 2-Chloro-2-phenyl-acetyl | 3% ½% | | | |
| Gamma Chloro-n-butryl | 3% ½% | | 5-0-5 4-0-5 | 5-0-5 5-5-2 |
| 3-Chloro-propionyl | 3% ½% | | | |
| 2-Bromo-propionyl | 3% ½% | | | |
| 3-Bromo-propionyl | 3% ½% | | | |

| | | Ethylene-diamine | 1,2-Dianilino-ethane | 1,8-Diamino-p-menthane |
|---|---|---|---|---|
| Dichloroacetyl | 3% ½% | 5-0-5 5-0-5 | 5-0-4 5-0-5 | 5-0-4 4-0-5 |
| Trichloroacetyl | 3% ½% | | | 5-0-5 4-3-3 |
| 2-Chloro propionyl | 3% ½% | 4-0-4 5-0-5 | | 5-0-5 5-0-5 |
| Dibromoacetyl | 3% ½% | | | 5-0-5 5-0-5 |
| 2-Bromo-butyryl | 3% ½% | | | |
| 2-Bromoiso-butyryl | 3% ½% | | | |
| 2-Chloro-2-phenyl-acetyl | 3% ½% | | | |
| Gamma Chloro-n-butryl | 3% ½% | | | |
| 3-Chloro-propionyl | 3% ½% | | | |
| 2-Bromo- | 3% | | | |

-continued

Evaluation of Amides as EPTC Antidote
(Ratings: emergence-abnormality-plant height)

| ACYL GROUP | | AMINE | | |
|---|---|---|---|---|
| propionyl | ½% | | | |
| 3-Bromo-propionyl | 3% ½% | | | |

| | | β-(4-Amino-phenyl)ethyl-amine | N-(2-Amino-propyl)cyclo-hexylamine | o-Phenyl-enediamine |
|---|---|---|---|---|
| Dichloroacetyl | 3% | 5-0-5 | 5-1-5 | 5-0-5 |
| | ½% | 5-0-5 | 4-0-5 | 5-0-5 |
| Trichloroacetyl | 3% | | | |
| | ½% | | | |
| 2-Chloro propionyl | 3% | | 5-0-5 | 5-0-5 |
| | ½% | | 3-0-5 | 5-0-5 |
| Dibromoacetyl | 3% | | | 5-0-5 |
| | ½% | | | 5-3-4 |
| 2-Bromo-butyryl | 3% ½% | | | |
| 2-Bromoiso-butyryl | 3% ½% | | | |
| 2-Chloro-2-phenyl-acetyl | 3% ½% | | | |
| Gamma Chloro-n-butryl | 3% | | | 5-0-5 |
| | ½% | | | 5-0-5 |
| 3-Chloro-propionyl | 3% ½% | | | |
| 2-Bromo-propionyl | 3% ½% | | | |
| 3-Bromo-propionyl | 3% ½% | | | |

| | | 4-Chloro-m-phenylene diamine | 2,4-Diamino-toluene | m-Xylene-diamine |
|---|---|---|---|---|
| Dichloroacetyl | 3% | 5-0-5 | 4-0-3 | 5-0-5 |
| | ½% | 5-2-5 | 5-0-5 | 5-0-5 |
| Trichloroacetyl | 3% ½% | | | |
| 2-Chloro propionyl | 3% ½% | | | |
| Dibromoacetyl | 3% | | 5-0-5 | |
| | ½% | | 5-1-4 | |
| 2-Bromo-butyryl | 3% ½% | | | |
| 2-Bromoiso-butyryl | 3% ½% | | | |
| 2-Chloro-2-phenyl-acetyl | 3% ½% | | | |
| Gamma Chloro-n-butryl | 3% ½% | | | |
| 3-Chloro-propionyl | 3% ½% | | | |
| 2-Bromo-propionyl | 3% ½% | | | |
| 3-Bromo-propionyl | 3% ½% | | | |

| | | 2,6-Dichloro-p-phenylene diamine | 1,5-Diamino-naphthylene | 1,8-Diamino-naphthylene |
|---|---|---|---|---|
| Dichloroacetyl | 3% | 5-0-5 | 5-0-5 | |
| | ½% | 5-0-5 | 5-0-5 | |
| Trichloroacetyl | 3% | | 5-0-5 | |
| | ½% | | 5-0-5 | |
| 2-Chloro propionyl | 3% | | | 5-0-5 |
| | ½% | | | 5-0-5 |
| Dibromoacetyl | 3% | | | 5-0-5 |
| | ½% | | | 5-3-3 |
| 2-Bromo-butyryl | 3% ½% | | | |
| 2-Bromoiso-butyryl | 3% ½% | | | |
| 2-Chloro-2-phenyl-acetyl | 3% ½% | | | |
| Gamma Chloro-n-butryl | 3% ½% | | | |
| 3-Chloro-propionyl | 3% ½% | | | |
| 2-Bromo-propionyl | 3% ½% | | | |
| 3-Bromo-propionyl | 3% ½% | | | |

| | | 2,3-Diamino- | 2,4'-Di-amino- |
|---|---|---|---|

-continued

Evaluation of Amides as EPTC Antidote
(Ratings: emergence-abnormality-plant height)

| ACYL GROUP | | AMINE | | |
|---|---|---|---|---|
| | | pyridine | diphenyl | o-Tolidine |
| Dichloroacetyl | 3% | 4-0-4 | 5-0-5 | 5-0-5 |
| | ½% | 5-0-5 | 5-0-5 | 5-0-4 |
| Trichloroacetyl | 3% ½% | | | |
| 2-Chloro propionyl | 3% | 5-0-5 | | |
| | ½% | 5-0-5 | 5-0-5 | |
| Dibromoacetyl | 3% | 5-0-5 | 5-3-2 | |
| | ½% | 5-2-4 | | |
| 2-Bromo-butyryl | 3% ½% | | | 5-0-5 |
| 2-Bromoiso-butyryl | 3% ½% | | | 5-5-1 |
| 2-Chloro-2-phenyl-acetyl | 3% ½% | | | |
| Gamma Chloro-n-butryl | 3% | 5-0-5 | | |
| | ½% | 5-1-5 | | |
| 3-Chloro-propionyl | 3% ½% | | | |
| 2-Bromo-propionyl | 3% ½% | | | |
| 3-Bromo-propionyl | 3% ½% | | | |

| | | Phenyl-hydrazine | 2,4,6-Tri-chlorophenyl-hydrazine | 2-Hydroxy-ethyl-hydrazine |
|---|---|---|---|---|
| Dichloroacetyl | 3% | 5-0-5 | | |
| | ½% | 5-3-2 | | |
| Trichloroacetyl | 3% ½% | | | |
| 2-Chloro propionyl | 3% | 4-0-3 | 5-0-5 | 5-0-5 |
| | ½% | 5-0-5 | 5-3-4 | 5-0-5 |
| Dibromoacetyl | 3% ½% | | | |
| 2-Bromo-butyryl | 3% ½% | | | |
| 2-Bromoiso-butyryl | 3% ½% | | | |
| 2-Chloro-2-phenyl-acetyl | 3% ½% | | | |
| Gamma Chloro-n-butryl | 3% ½% | | | |
| 3-Chloro-propionyl | 3% ½% | | | |
| 2-Bromo-propionyl | 3% ½% | | | |
| 3-Bromo-propionyl | 3% ½% | | | |

| | | Oxamic hydrazide | N-Isopropyl benzylamine | 2,4-Dichloro-N-isopropyl-benzylamine |
|---|---|---|---|---|
| Dichloroacetyl | 3% | 5-0-5 | 0-0-0 | 2-0-5 |
| | ½% | 3-2-4 | 5-0-5 | 5-1-5 |
| Trichloroacetyl | 3% | 5-0-5 | | |
| | ½% | 3-2-4 | | |
| 2-Chloro propionyl | 3% ½% | | | |
| Dibromoacetyl | 3% ½% | | | |
| 2-Bromo-butyryl | 3% ½% | | | |
| 2-Bromoiso-butyryl | 3% ½% | | | |
| 2-Chloro-2-phenyl-acetyl | 3% ½ | | | |
| Gamma Chloro-n-butryl | 3% ½% | | | |
| 3-Chloro-propionyl | 3% ½% | | | |
| 2-Bromo-propionyl | 3% ½% | | | |
| 3-Bromo-propionyl | 3% ½% | | | |

| | | 1,2,3,4-Tetra hydroiso-quinoline | N-Isopropyl-4-nitro-benzylamine | |
|---|---|---|---|---|
| Dichloroacetyl | 3% | 5-0-4 | 5-0-5 | |
| | ½% | 5-0-5 | 5-0-5 | |
| Trichloroacetyl | 3% ½% | | | |

-continued

Evaluation of Amides as EPTC Antidote
(Ratings: emergence-abnormality-plant height)

| ACYL GROUP | | AMINE | |
|---|---|---|---|
| 2-Chloro propionyl | 3% ½% | | |
| Dibromoacetyl | 3% ½% | | |
| 2-Bromo-butyryl | 3% ½% | | |
| 2-Bromoiso-butyryl | 3% ½% | | |
| 2-Chloro-2-phenyl-acetyl | 3% ½% | | |
| Gamma Chloro-n-butryl | 3% ½% | | |
| 3-Chloro-propionyl | 3% ½% | | |
| 2-Bromo-propionyl | 3% ½% | | |
| 3-Bromo-propionyl | 3% ½% | | |

| | | N-Allyl-3-chloro-benzylamine | 3-Methylmer-captoaniline |
|---|---|---|---|
| Dichloroacetyl | 3% | 5-0-5 | |
| | ½% | | 5-0-5 |
| Trichloroacetyl | 3% ½% | | |
| 2-Chloro propionyl | 3% ½% | | |
| Dibromoacetyl | 3% ½% | | |
| 2-Bromo-butyryl | 3% ½% | | |
| 2-Bromoiso-butyryl | 3% ½% | | |
| 2-Chloro-2-phenyl-acetyl | 3% ½% | | |
| Gamma Chloro-n-butryl | 3% ½% | | |
| 3-Chloro-propionyl | 3% ½% | | |
| 2-Bromo-propionyl | 3% ½% | | |
| 3-Bromo-propionyl | 3% ½% | | |

B. Protection of Inbred Lines of Zea Mays

At rates as low as 1/16% by weight on corn seed, 1,8-naphthalic anhydride is sufficiently phytotoxic to certain inbred strains of corn that it will not only injure the corn but fail to protect it from herbicides such as EPTC, so that the corn will die. For example, the inbred line, Micigan State 1334 is killed when treated with naphthalic anhydride but is effectively protected from EPTC without injurious side effects by application to the seed of an effective amount of N-dichloroacetyl-1,2,3,4-tetrahydroisoquinoline. The practice of this embodiment of the invention enables growers of hybrid seed corn to protect their inbred seed lines from herbicides.

C. Protection of Rice

1. Chemical Preparation

Under "purity" in the following table are the designations Pure, R.P. and 50%. These are respectively; pure as indicated R.P. indicates the reaction product of 1 molar proportion of acid chloride with two molar proportions of the amine; 50% indicates application as a dust containing 50% inert solid diluent. In certain products in which the reaction product may be in doubt it is not identified by name. N-Cyclopropyldichloroacetamide was employed both pure and as a 50% dust. In one case methanol was used with the 50% dust as a solvent to promote better coating and adherence; in comparative tests, no methanol was used.

2. Seed Treatment Method 5 g. Saturn rice in a 3 dram vial was treated with the chemical at the indicated rate along with 1 vol. percent methanol per unit weight and was shaken 20 sec. in a Spex. mixer.

3. Soil Treatment 20 seeds of each lot were planted in a row in greenhouse flats, lightly covered with soil and treated with 4 lb/A S-ethyl N,N-diethylthiocarbamate or 6 lb/A molinate. Additional soil was used to cover the chemical.

Duplicate tests were made with some of the protection agents. These give an indication of repeatability of the tests. Data on the herbicide treated checks are based on 120 seeds and untreated check data are based on 720 seeds. Data were taken 24 days after planting. Results are tabulated below.

PROTECTION OF RICE

| PURITY | COMPOUND NAME OR STARTING MATERIALS | S-Ethyl-N,N-diethyl-thiocarbamate | | | Molinate | | |
|---|---|---|---|---|---|---|---|
| | | Appln. Rate wt. % | Stand % | Height (in.) | Appln. Rate Wt. % | Stand % | Height (in.) |
| Purified | N-cyclopropyldichloroacetamide | 5/16 | 95 | 7 | 5/32 | 45 | 10 |
| R.P. | N,N,-dipropargyl-2-bromo-butyrylamide | 1/2 | 70 | 10 | 1 | 40 | 14 |
| R.P. | N-2-Butyltribromoacetamide | 5/32 | 65 | 6 | 5/16 | 40 | 12 |
| Pure | N-Benzyldichloroacetamide | 1/40 | 45 | 4 | 1 | 30 | 9 |
| Pure | N,N-Dimethyldichloroacetamide | 1/2 | 85 | 9 | 1 | 75 | 14 |
| R.P. | N-isopentyldichloroacetamide | 1/4 | 85 | 10 | 1/8 | 25 | 8 |
| R.P. | N-Methyldichloroacetamide | 1/2 | 85 | 6 | 1 | 55 | 13 |
| R.P. | Ethylenediamine + dichloroacetylchloride | 2 | 75 | 6 | 1 | 40 | 12 |
| R.P. | N(2-Benzyloxy)ethyl-dichloroacetamide | 1/2 | 75 | 11 | 1/2 | 55 | 17 |
| R.P. | 2,5-Dimethylpyrrole and dichloroacetyl chloride | 5/16 | 80 | 9 | 5/8 | 50 | 15 |
| R.P. | N-3-Isopropoxypropyl-dichloroacetamide | 1 1/4 | 65 | 8 | 5/8 | 70 | 14 |
| R.P. | N-(2-P-cymene)-dichloroacetamide | 5/8 | 65 | 11 | 5/8 | 50 | 12 |
| R.P. | N-(2-Chloro-5-trifluoromethyl)-dichloroacetanilide | 1/2 | 75 | 5 | 1/2 | 60 | 14 |
| R.P. | N-Furfuryldichloroacetamide | 5/16 | 80 | 4 | 5/16 | 60 | 11 |
| R.P. | N-Methyl-N-tetrahydrofurfuryl-dichloroacetamide | 1/2 | 75 | 13 | 1/2 | 35 | 9 |
| R.P. | N-Dichloroacetylmorpholine | 5/8 | 75 | 18 | 5/8 | 70 | 12 |
| R.P. | N-Ethyldichloroacetamide | 5/8 | 75 | 7 | 5/8 | 35 | 10 |
| R.P. | N-m-methyldichloroacetanilide | 5/8 | 45 | 6 | 5/32 | 20 | 8 |
| R.P. | N'o-Chlorobenzyl-N-methyl-dichloroacetamide | 5/32 | 55 | 5 | 5/16 | 20 | 6 |
| R.P. | 2,5-Dimethylpyrrole and | 5/8 | 50 | 10 | 5/8 | 25 | 6 |

-continued

PROTECTION OF RICE

| PURITY | COMPOUND NAME OR STARTING MATERIALS | S-Ethyl-N,N-diethyl-thiocarbamate | | | Molinate | | |
|---|---|---|---|---|---|---|---|
| | | Appln. Rate wt. % | Stand % | Height (in.) | Appln. Rate Wt. % | Stand % | Height (in.) |
| Pure | Trichloroacetylchloride N-Cyclopropyldichloroacetamide | 5/32 | 95 | 7 | 5/32 | 70 | 9 |
| 50% dust | N-Cyclopropyldichloro-acetamide with methanol | 1 1/4 | 90 | 7 | 1 1/4 | 60 | 9 |
| 50% dust | N-Cyclopropyldichloroacetamide | 1 1/4 | 85 | 6 | 5/16 | 35 | 9 |
| Pure | 1,8-Naphthalic anhydride | 1/2 | 70 | 9 | 1/2 | 50 | 17 |
| R.P. | n-p-fluoro-alpha-methylbenzyl dichloroacetamide | 1/2 | 40 | 4 | 1/8 | 25 | 10 |
| R.P. | 2,5-Dimethylpyrrole and dichloroacetyl chloride | 5/8 | 65 | 10 | 5/8 | 25 | 10 |
| R.P. | N-3-isopropoxypropyl-dichloroacetamide | 5/16 | 60 | 9 | 5/16 | 25 | 10 |
| R.P. | N-methyl-N-butyldichloroacetamide | 5/32 | 40 | 7 | 5/32 | 35 | 10 |
| Check | (no protective agent) | | 5 | 2 | | 1 | 6 |
| Untreated | (neither herbicide nor protective agent) | | 82 | 20 | | | |

When considered with regard to both neight and percent stand, the protective effect of N-cyclopropyldichloroacetamide was outstanding.

PROTECTION OF OTHER CROPS

Generally high effectiveness and freedom from injurious side effects enable the dichloroacetamides to be employed to protect a variety of grain crops from a number of thiocarbamate and amide type pre-emergent herbicides.

For example, N-dichloroacetyl-1,2,3,4-tetrahydroisoquinoline is effective in protecting grain sorghum from alachlor and protecting rice from molinate. Illustrative examples of other herbicides from which various grain crops are protected are butylate, cycloate, diallate, triallate, pebulate, vernolate, chloramben, barban, trifluoralin and 2,4-D.

The versatility of some of the chemical agents with regard to protection of several crops from various herbicides was demonstrated by means of a test involving fifteen crops and eight herbicides, as described below.

A mixture of seeds of 15 crops (rice, oats, rye, barley, cotton, wheat, corn, peas, soybeans, cabbage, grain sorghum, sugar beets, alfalfa, tomato and flax) weighing approximately six grams in a 3 dram vial was treated in each instance with the indicated quantity of chemical and 1 wt percent methanol per unit weight, was shaken 20 sec. in a Spex mixer, planted in greenhouse flats and covered lightly with soil. Herbicides were applied at the indicated rates. Additional soil was then added to cover the herbicide. After 12 to 15 days protective activity, where observed, was recorded and appears as a plus sign in the table which follows.

Chemicals selected for this test had already shown an ability to protect corn from EPTC.

Under "purity" in the tables, "pure" indicates that the compound had been purified. "R.P." indicates that crude, unpurified reaction product was used, as in the tests on rice described above.

| Purity | Rate % | Chemical | 2-Chloro-2'6'-diethyl-N-butoxymethyl-acetanilide (4 lb/A) | | | Alachlor (4 lb/A) | | Molinate (6 lb/A) | | S-Ethyl N,N-diethyl-thiocarbamate (4 lb/A) |
|---|---|---|---|---|---|---|---|---|---|---|
| | | | Corn | Rice | Grain Sorghum | Corn | Grain Sorghum | Rice | Corn | Rice |
| Pure | 1/2 | N-Benzyldichloro-acetamide | | + | + | + | + | + | + | + |
| Pure | 1/4 | N,N-Dibenzyldichloro-acetamide | | + | | + | | | + | |
| Pure | 1/2 | 2,6-Dimethyldichloro-acetanilide | | | | + | | | + | |
| Pure | 1/4 | N-3,4-Dichlorobenzyl-dichloroacetamide | + | + | + | + | | | + | |
| Pure | 1/4 | N-Dichloroacetyl-cycloheptylimine | | + | + | + | + | | + | |
| Pure | 1/4 | N-Cyclohexylenethyl-dichloroacetamide | ± | ± | + | | | | + | |
| Pure | 1/4 | N,N-Dimethyldichloro-acetamide | | + | + | + | | | + | |
| Pure | 1/8 | N,N-Diisopentyldi-chloroacetamide | | | | + | | | + | |
| Pure | 1/2 | 2,6-Diethyldi-chloroacetanilide | + | + | | + | | | + | |
| Pure | 1/4 | N-Cyclohexyl-dichloro-acetamide | | | | + | | | + | |
| Pure | 1/4 | N-Isopropyl-N-benzyltrichloro-acetamide | + | + | | + | | | + | |
| Pure | 1/16 | N-Isopropyl-N-benzyldichloro-acetamide | | | + | + | | | + | |
| R.P. | 1/2 | 2,2,6,6-Tetra-methylpiperidine-and 2-Chloro- | + | + | | + | | | + | + |

| Purity | Rate % | Chemical | 2-Chloro-2'6'-diethyl-N-butoxymethyl-acetanilide (4 lb/A) | | | Alachlor (4 lb/A) | | Molinate (6 lb/A) | | S-Ethyl N,N-diethyl-thiocarbamate (4 lb/A) |
|---|---|---|---|---|---|---|---|---|---|---|
| | | | Corn | Rice | Grain Sorghum | Corn | Grain Sorghum | Rice | Corn | Rice |
| | | acetyl chloride | | | | | | | | |
| Pure | 1/4 | N-Benzyl-N-methyl-dichloroacetamide | | | | + | | | + | |
| Pure | 1/4 | N-3-Chlorobenzyl-trichloroacetamide | + | | | + | | | + | |
| R.P. | 1/4 | N,N-Dimethyl-2-chloropropionamide | + | | | + | | | + | |
| R.P. | 1/8 | N-Isobutyl-2-chloropropionamide | + | | | + | | | + | |
| R.P. | 1/8 | N-dl-2-methylbenzyl-dichloroacetamide | + | | | + | | | + | |
| R.P. | 1/4 | N-p-Fluoro-2-methyl-benzyldichloroacetamide | + | | + | + | + | | + | |
| Pure | 5/32 | N,N-Dipropylidichloroacetamide | + | | | + | | | + | |
| Pure | 5/16 | N-t-butyldichloroacetamide | + | | | + | | | + | |
| Pure | 5/16 | N-Cyclopropyldichloroacetamide | + | + | | + | + | + | + | + |
| R.P. | 5/16 | N-Cyclopropyltrichloroacetamide | + | | | + | | | + | |
| R.P. | 5/32 | N-Isopropyl-N-cyclohexyldichloroacetamide | + | | | + | | | + | |
| R.P. | 5/16 | N-t-Butyltribromoacetamide | + | + | + | + | + | | + | + |
| R.P. | 5/8 | p-Phenylenediamine and dichloroacetyl chloride | + | + | | + | + | | + | |
| R.P. | 5/32 | Isopropyldichloroacetamide | + | | | + | | | + | + |
| R.P. | 5/16 | Piperidine and dichloroacetyl chloride | + | + | | + | | | + | |
| R.P. | 5/8 | 2,5-Dimethylpyrrole and dichloroacetyl chloride | | | | + | | + | + | + |
| R.P. | 5/16 | N-methyl-N-butyl-dichloroacetamide | | | + | + | | | + | + |
| R.P. | 5/8 | N-3-Isopropoxypropyl-dichloroacetamide | | | + | + | | + | + | + |
| Pure | 1/2 | N-Propargyldichloroacetamide | | | | + | | | + | + |
| Pure | 1/2 | N-1,3-Dimethylpentyl-chloroacetamide | | | | + | + | + | + | |
| Pure | 1/4 | N-Isobutyltrichloroacetamide | | | | + | | + | | |
| R.P. | 1/2 | N,N-Dipropargyl-2-bromobutyramide | | | | + | + | | + | |
| R.P. | 1/8 | N,N-Dipropargyl-2-bromobutyramide | | | | + | + | | + | |
| R.P. | 1/8 | N-Isopentyldichloroacetamide | | | | + | | | + | + |
| R.P. | 5/16 | N-(2-p-Cymene)dichloroacetamide | | | | + | | | + | + |
| R.P. | 5/16 | 2,3-Diaminopyridine and dichloroacetyl chloride | | | | + | | | + | + |
| R.P. | 5/32 | N-Furfuryldichloroacetamide | | | | + | | | + | + |
| R.P. | 5/8 | 4-Methoxy-2-methyl-dichloroacetanilide | | | | + | | | + | |
| R.P. | 5/8 | 2-Methoxy-2-methyl-dichloroacetanilide | | | | + | | | + | |
| R.P. | 5/16 | N-Dichloroacetyl-morpholine | | | | + | | | + | + |
| R.P. | 5/8 | N-Ethyldichloroacetamide | | | | + | | + | + | + |
| R.P. | 5/16 | m-Methyldichloroacetanilide | | | | + | | | + | + |
| R.P. | 5/16 | N-O-Chlorobenzyl N-methyldichloroacetamide | | | | + | | | + | + |
| R.P. | 5/16 | 2,5-Dimethylpyrrole and trichloroacetyl chloride | | | | + | | + | + | + |
| R.P. | 1/2 | N-Methyldichloroacetamide | | | | + | | | + | + |
| R.P. | 1 | Ethylenediamine + dichloroacetyl chloride | | | | + | | | + | + |
| R.P. | 1/8 | 3-Chloro-2-methyl-dichloroacetanilide | | | | + | | | + | |
| R.P. | 1 | N-Dichloroacetyl-4-aminomethyl pyridine | | | | + | + | | + | |
| R.P. | 1/4 | N-Allyl-N-Phenyl-dichloroacetamide | | | | + | | | + | |
| R.P. | 1/4 | N-Allyl-N-(o-methylphenyl)dichloroacetamide | | | | + | | | + | |
| R.P. | 1 | 3-Aminothiophenol and | | | | + | | | + | |

-continued

| Purity | Rate % | Chemical | 2-Chloro-2'6'-diethyl-N-butoxymethyl-acetanilide (4 lb/A) | | | Alachlor (4 lb/A) | | Molinate (6 lb/A) | | S-Ethyl N,N-diethyl-thiocarbamate (4 lb/A) |
|---|---|---|---|---|---|---|---|---|---|---|
| | | | Corn | Rice | Grain Sorghum | Corn | Grain Sorghum | Rice | Corn | Rice |
| | | dichloroacetyl chloride | | | | | | | | |
| R.P. | 1/4 | N-(2-Benzyloxy)ethyl-dichloroacetanilide | | | | + | | | + | |
| R.P. | 1/4 | 3-Methylmercaptodichloroacetanilide | | | | + | | | + | |
| R.P. | 1/2 | 2,4-Diaminotoluene and dichloroacetyl chloride | | | | | | | | |
| R.P. | 1/2 | N-(2-Chloro-5-trifluoromethyl)dichloroacetanilide | | | | | + | | | + |
| R.P. | 1/8 | 4-Iododichloroacetanilide | | | | | | | | |
| R.P. | 1/4 | 3-Fluorodichloroacetanilide | | | | | | | + | |
| R.P. | 1/2 | 2-Ethyldichloroacetanilide | | | | | | | + | |
| R.P. | 1/2 | 1-Naphthyl-5,6,7,8-tetrahydrodichloroacetamide | | | | | | | | |
| R.P. | 1/2 | N-Methyl-N-Tetrahydrofurfuryldichloroacetamide | | | | | | + | + | + |

I claim:

1. The method of protecting rice seed comprising applying thereon a coating of an effective but substantially non-phytotoxic quantity of an amide of dichloroacetic acid sufficient to improve resistance of the rice to a pre-emergent thiolcarbamate herbicide.

* * * * *